(12) United States Patent
Zhang et al.

(10) Patent No.: US 8,287,901 B2
(45) Date of Patent: Oct. 16, 2012

(54) WOUND HEALING COMPOSITIONS BASED ON CYANOACRYLATES AND 5,5-DISUBSTITUTEDHYDANTOINS, INCLUDING PHENYTOIN

(75) Inventors: Sheng Zhang, Granite Falls, NC (US); Rafael Ruiz, Sr., Hudson, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 61 days.

(21) Appl. No.: 12/854,243

(22) Filed: Aug. 11, 2010

(65) Prior Publication Data

US 2012/0039838 A1 Feb. 16, 2012

(51) Int. Cl.
*A61F 13/02* (2006.01)
*A61L 15/16* (2006.01)
*A61K 31/74* (2006.01)
*C08G 73/06* (2006.01)

(52) U.S. Cl. ............ 424/448; 424/78.06; 528/423
(58) Field of Classification Search ............ 424/448, 424/78.06; 528/423
See application file for complete search history.

(56) References Cited

U.S. PATENT DOCUMENTS

| | | | |
|---|---|---|---|
| 2,721,858 A | 10/1955 | Joyner et al. | |
| 3,254,111 A | 5/1966 | Hawkins et al. | |
| 5,684,042 A | 11/1997 | Greff et al. | |
| 5,762,919 A | 6/1998 | Greff et al. | |
| 5,783,177 A | 7/1998 | Greff et al. | |
| 5,811,091 A | 9/1998 | Greff et al. | |
| 6,214,332 B1 | 4/2001 | Askill et al. | |
| 6,316,523 B1 * | 11/2001 | Hyon et al. | 523/111 |
| 2005/0042266 A1 | 2/2005 | Narang | |
| 2006/0188486 A1 | 8/2006 | Carpenter et al. | |
| 2007/0299043 A1 | 12/2007 | Hunter et al. | |
| 2009/0022779 A1 * | 1/2009 | Kelly et al. | 424/445 |
| 2009/0317353 A1 | 12/2009 | Zhang et al. | |
| 2009/0318583 A1 | 12/2009 | Zhang et al. | |

FOREIGN PATENT DOCUMENTS

WO   WO2010/008822 A2   1/2010
WO   WO2010/008822 A3   1/2010

OTHER PUBLICATIONS

Quinn et al. ("A Randomized Trial Comparing Octylcyanoacrylate Tissue Adhesive and Sutures in the Management of Lacerations" in JAMA vol. 277, No. 19, pp. 1527-1530 (May 21, 1997).*
Simon et al., ("Lacerations Against Langer's Lines: To Glue or Suture" in Journal of Emrgency Medicine vol. 16, No. 2, pp. 185-189 (1998).*
Pendse et al., ("Topical Phenytoin in Wound Healing" in International Journal of Dermatology vol. 32, No. 3, pp. 214-217, Mar. 1993).*
Talas et al., ("Role of Phenytoin in Wound Healing—A Wound Pharmacology Perspective" in Biochemical Pharmacology vol. 57, pp. 1085-1094 (1999).*
Naeini et al., ("Effects of Topical and Parenteral Application of Phenytoin on Cutaneous Wound Healing in Rabbits" in Journal of Animal and Veterinary Advances 7(12), pp. 1537-1545 (2008).*
Shapiro ("Acceleration of Gingival Wound Healing in Non-Epileptic Patients Receiving Diphenylhydantoin Sodium (Dilantin, Epanutin)" in Exp. Med. Surg. 16 (1), pp. 41-53 (1958).*
International Search Report and Written Opinion issued Jan. 9, 2012 for corresponding international patent application No. PCT/US2011/047090.
Bhatia et al., "Topical Phenytoin for Wound Healing" Dermatology Online Journal, vol. 10, No. 1: 5 (2004) 6 pages as downloaded from http://dermatology-s10.cdlib.org/101/reviews/phenytoin/bhatia.html.
Naeini et al., "Effects of Topical and Parenteral Application of Phenytoin on Cutaneous Wound Healing in Rabbits" Journal of Animal and Veterinary Advances 7(12), pp. 1537-1545 (2008).
Pendse et al., "Topical Phenytoin in Wound Healing" International Journal of Dermatology vol. 32, No. 3, pp. 214-217, Mar. 1993.
Quinn et al, "A Randomized Trial Comparing Octylcyanoacrylate Tissue Adhesive and Sutures in the Management of Lacerations" JAMA vol. 277, No. 19, pp. 1527-1530 (May 21, 1997).
Scheinfeld, "Phenytoin in Cutaneous Medicine: Its Uses, Mechanisms and Side Effects" Dermatology Online Journal vol. 9, No. 3: 6 2003 (17pages) downloaded from http://dermatology-s10.cdlib.org/93/reviews/dilantin/scheinfeld.html.
Shapiro, "Acceleration of Gingival Wound Healing in Non-Epileptic Patients Receiving Diphenylhydantoin Sodium (Dilantin, Epanutin)" Exp. Med. Surg. 16(1), pp. 41-53 (1958).
Simon et al., "Lacerations Against Langer's Lines: to Glue or Suture?" Journal of Emergency Medicine vol. 16, No. 2, pp. 185-189 (1998).
Talas et al., "Role of Phenytoin in Wound Healing—A Wound Pharmacology Perspective" Biochemical Pharmacology vol. 57, pp. 1085-1094 (1999).

* cited by examiner

*Primary Examiner* — Blessing Fubara
(74) *Attorney, Agent, or Firm* — Stradley Ronon Stevens & Young, LLP

(57) ABSTRACT

A monomeric adhesive composition includes a stabilized polymerizable monomer, such as a 1,1-disubstituted monomer, including a cyanoacrylate, and a wound healing agent, wherein the wound healing agent is 5,5-disubstitutedhydantoin, including phenyloin; and a method for making said composition.

11 Claims, No Drawings

WOUND HEALING COMPOSITIONS BASED ON CYANOACRYLATES AND 5,5-DISUBSTITUTEDHYDANTOINS, INCLUDING PHENYTOIN

FIELD OF THE INVENTION

The present invention is directed to a stable, sterilizable liquid adhesive composition containing a wound healing accelerator, a 5,5-disubstitutedhydantoin, including phenyloin, and the method for making such compositions for industrial and medical uses.

BACKGROUND OF THE INVENTION

Wound management has been one of the most challenging tasks for medical professionals.

In the past, many wound healing agents and methods for local wound management have been developed. Some of the traditional wound healing agents, though now less widely used, are still beneficial in certain clinical settings for wound treatment. Such wound healing methods include liquid or semi-solid formulations of povidone-iodine, silver, and polyhexamethylene biguanide used topically or incorporated into dressings to promote wound healing. Additional traditional approaches to wound healing include physiological saline solution, silver nitrate ointment, and dressings including gauze, cotton, wool, and synthetic or natural bandage.

Most of the traditional wound healing methods have been replaced by modern wound management techniques and increasingly more studies have been dedicated to develop methods and agents to promote wound healing.

Topical application of biologically active compounds has been proven to be an effective method for promoting wound healing. These active compounds include growth factors, mitogens, and hormones. However, such applications are limited in that it is difficult to regulate the dosage of the active compounds and the compounds rapidly degrade. For example, U.S. Patent Application Publication No. 20060188486 to Carpenter et al. discloses wound healing polymer compositions that release a wound healing agent at a controlled rate. The wound healing agents disclosed include proteinaceous growth factors, vascular endothelial growth factors, anti-proliferant agent, antimicrobials, anti-inflammatory agents, tissue grafts and wound healing cells.

One of the most popular techniques among modern methods for promoting wound healing is the application of monomer and polymer tissue adhesives. Included among these adhesives are the 1,1-disubstituted ethylene monomers and polymers, such as the alpha-cyanoacrylates. Since the discovery of the adhesive properties of such monomers and polymers, they have found wide use due to the speed with which they cure, the strength of the resulting bond formed, and their relative ease of use. These characteristics have made alpha-cyanoacrylate adhesives the primary choice for numerous applications even outside the medical arena, including industrial and home use in bonding plastics, rubbers, glass, metals, and wood.

Tissue adhesives have been investigated extensively as the healing agent for topical wounds. Compared to suture and other wound closure agents, cyanoacrylate adhesives demonstrate similar cosmetic results, but more importantly, improve the rate of wound closure (Quinn et al. *JAMA*, 277, 1527-30, 1997). It has also been found that cyanoacrylate tissue adhesives can be the preferred method in terms of cosmetic appearance for the cutaneous closure of facial lacerations (Simon et al. *J. Emerg. Med.* 16, 185, 1998). Besides faster wound closure and better cosmesis, advantages of cyanoacrylate adhesives over suture or staples also include lower infection rates. And, the recently FDA approved and commercially available SurgiSeal® topical skin adhesive, which is a 2-octylcyanoacrylate, has shown a desirable water vapor transmission rate (WVTR) which could be beneficial to wound healing. (SurgiSeal® topical skin adhesive is manufactured by Adhezion Biomedical, LLC, Wyomissing, Pa.)

Although the source for this characteristic is not understood it has been observed that cyanoacrylate compositions inherently possess some antimicrobial activity. In particular, cyanoacrylate compositions themselves are believed to prevent the growth of some types of microorganisms within the compositions. But because this property is limited, in order to further enhance wound healing using cyanoacrylate adhesives, different wound healing agents have been incorporated into cyanoacrylate tissue adhesives. For example, U.S. Patent Application Publication No. 20050042266 to Narang and U.S. Pat. Nos. 5,684,042, 5,762,919, 5,811,091 and 5,783,177 to Greff et al. disclose that an effective amount of antimicrobial agents can be incorporated into cyanoacrylate adhesive compositions to promote wound healing.

U.S. Pat. No. 6,214,332 to Askill et al. discloses antimicrobial cyanoacrylate ester compositions which may further include medicaments, such as growth factors such as epidermal growth factor, platelet derived growth factor, transforming growth factors, keratinocyte growth factor and fibroblast growth factor. However, as a general matter, it has been a challenging task to incorporate medicaments into cyanoacrylate adhesives. Most medicaments are not soluble in cyanoacrylates. Additionally, many if not most medicaments negatively affect the polymerization rate of the monomer composition, either by acting as inhibitors or as initiators. Thus, the cyanoacrylate could be prevented from curing (polymerizing) or induced to prematurely polymerize resulting in an undesirable reduction or destruction of the shelf-life stability of the cyanoacrylate. Additionally, incorporation of medicaments could also affect the viscosity of the composition and the resulting performance of the cyanoacrylate in terms of cure time and bonding strength. In addition, medicaments based on protein could be inactivated due to the binding of protein to cyanoacrylate, as U.S. Pat. No. 5,684,042 to Greff et al. discloses. Therefore, better methods and compositions are still needed with regard to promoting wound healing.

Another wound healing accelerator is phenyloin. Phenyloin refers to diphenylhydantoin or 5,5-diphenylimidazolidine-2,4-dione, which originally was introduced into therapy in 1937 as an effective anticonvulsant in the treatment of epileptic patients. It has been noted that a common side effect of phenyloin treatment for seizures is the development of fibrous overgrowth of gingival (gums). It is believed that this occurs by the phenyloin stimulating responsive sub-population of fibroblasts to synthesize the increased amount of collagen. The great potential of phenyloin in wound healing is thus derived from the obvious stimulatory effect of phenyloin on connective tissue.

U.S. Patent Application Publication No. 20090022779 to Kelly et al. discloses gel-based phenyloin formulations suitable for topical application to wound sites. The disclosed compositions contain phenyloin dissolved in an aqueous component of gel and solid powder which entraps the phenyloin. The gelling agent can be selected from alginic acid, chitosan and its derivatives, and a carbomer.

In vivo and clinical studies have demonstrated that topical phenyloin provides advantages as a wound healing agent. A controlled clinical trial, using phenyloin by applying it to periodontal patients with surgical wounds, reported that phenyloin accelerated wound healing and reduced inflammation and pain (Shapiro, *Exp. Med. Surg.* 16, 41-53, 1958). Furthermore, a large number of clinical studies concluded that phenyloin therapy has a beneficial effect on healing of various wound types including surgical wounds, burns, pressure ulcers, traumatic wounds, decubitus ulcers, venous stasis ulcers, and diabetic ulcers, many of which are difficult and chronic wounds (Naeini et al. *J. Anim. Vet. Adv.* 12, 1537-1545, 2008; Talas et al. *Biochem. Pharmacol.* 57, 1085-1094, 1999; Bhatia et al., *Dermatol. Online J.* 10, 5, 2004; Scheinfeld *Dermatol. Online J.* 9, 6, 2003). It is believed that phenyloin has a stimulatory effect on tissue growth by improving granulation tissue formation which is beneficial to wound healing.

Besides enhancing wound healing, phenyloin has an antimicrobial property and has been shown to decrease the bacterial load of wounds as proved by a number of clinical studies (Pendse et al. *Int. J. Dermatol.* 32, 214-7, 1993). In addition, topical phenyloin therapy can relieve local pain when applied onto the wound site due to its membrane-stabilizing property thereby providing rapid relief for patient's comfort. Additionally, phenyloin can reduce inflammation and wound transudation. And, as a wound healing agent, phenyloin could possibly accelerate nerve regeneration. Other advantages are that phenyloin is safe to use, cost effective and readily available as opposed to expensive alternatives such as a mixture of synthetic growth factors.

Considering the established efficacy of phenyloin in promoting wound healing, there is a clear need for methods through which the effective wound healing property of phenyloin may be provided in a convenient, stable, efficacious and reproducible manner to local wounds.

A need also exists for improved adhesive compositions, especially for medical uses, that contain medicaments, but where the performance of the adhesive composition is not compromised.

SUMMARY OF THE INVENTION

The present invention provides sterilizable, stable, polymerizable cyanoacrylate compositions containing a 5,5-disubstitutedhydantoin wound healing accelerator, including phenyloin, for use in the medical field.

The instant inventors have discovered a novel composition incorporating a 5,5-disubstitutedhydantoin wound healing accelerator into cyanoacrylate adhesives enabling the accelerator to be delivered and released to a wound site during the process of wound closure and/or healing. This unique combination of the desirable characteristics of both cyanoacrylate adhesive film and 5,5-disubstitutedhydantoins to heal wounds will provide enhanced wound healing effects not experienced heretofore and a superior technique for wound management.

The instant invention realizes the combined benefits of both cyanoacrylate adhesives and 5,5-disubstitutedhydantoins. The naturally antibacterial characteristic of cyanoacrylate in addition to its wound sealing and physical film barrier properties is enhanced by the tissue growth stimulating, antimicrobial, anesthetic, and anti-inflammatory properties of one compound, a 5,5-disubstitutedhydantoin, especially phenyloin.

After topically applying to wounds or incisions, the inventive cyanoacrylate adhesives cure to form polymer films that provide a controlled and slow release of the accelerator medicament.

Production of the sterilized composition includes placing a homogeneous solution of stabilized polymerizable monomer and the wound healing agent in a container, sealing the container and sterilizing the container and the mixture. The compositions produced, packaged and sterilized according to the present invention are stable, and have extended utility, as compared to adhesive compositions of the prior art.

The present invention also provides a method for homogenously incorporating the healing accelerator into liquid cyanoacrylate monomer adhesive compositions without inducing the premature polymerization of such adhesives. The combination of heating the heterogeneous mixture of healing accelerator and cyanoacrylate compositions to an elevated temperature and stabilizing the cyanoacrylate monomer with desirable stabilizers prior to incorporation of the accelerator ("pre-stabilizing"), results in a stable and homogeneous solution of cyanoacrylate containing 5,5-disubstitutedhydantoin. The resulting cyanoacrylate compositions containing the healing accelerator can also be sterilized and exhibit an extended shelf life.

The present invention also provides a kit for applying the sterilized cyanoacrylate adhesive compositions, including an applicator and cyanoacrylate formulations containing a 5,5-disubstitutedhydantoin as the wound healing accelerator.

Also provided is a method of applying the sterilized liquid inventive wound healing cyanoacrylate compositions to tissue, and the resulting film.

DETAILED DESCRIPTION OF PREFERRED EMBODIMENTS

The invention relates to formulations and methods for treating wounds. The present invention provides a formulation of cyanoacrylate monomers containing a wound healing accelerator, 5,5-disubstitutedhydantoin, including phenyloin. Also provided is a method for incorporating the healing accelerator into cyanoacrylate monomers by heating the heterogeneous mixture of accelerator and cyanoacrylate monomers to a mildly elevated temperature. The formulations containing both cyanoacrylate monomers and healing accelerator are pre-stabilized with suitable amounts of the desirable polymerization inhibitors. The said formulations are sterilized with suitable sterilization methods so that cyanoacrylate formulations containing the 5,5-disubstitutedhydantoin can be used in the medical field for the treatment of wounds, including wound closure and for the improvement of wound healing. According to the preferred embodiments of the present invention, the sterilized cyanoacrylate formulations containing 5,5-disubstitutedhydantoin can provide a long term stable shelf life of at least 2 years.

It is believed that the compositions of the present invention are suitable for use in a variety of medical settings but should be particularly applicable in a surgical setting to promote the healing process of surgical incisions. In addition, it is contemplated that such compositions based on both cyanoacrylate and 5,5-disubstitutedhydantoin can be most beneficial in the treatment of chronic wounds or those which are resistant to healing. According to the present invention, it is expected that this composition having the wound healing activity of the accelerator in combination with the effects of the wound sealing ability, and other known benefits, of cyanoacrylates will provide for overall improved wound healing. After topically applying to the wounds or surgical incisions, the liquid cyanoacrylate adhesives are cured to form polymer films with tissue growth stimulating, antimicrobial and mechanical barrier properties. By incorporating 5,5-disubstitutedhydantoin within a cyanoacrylate polymer, a controlled and slow release of the accelerator medicament can be achieved.

The wound healing agent or accelerator is a 5,5-disubstitutedhydantoin as set forth in Formula I below, wherein R is any alkyl or aromatic group, preferably an un-substituted or substituted phenyl group. Each R substituent may be the same or different.

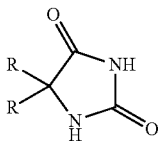

Formula I

The preferred accelerator is 5,5-diphenylhydantoin also known as phenyloin, 5,5-diphenyl-2,4-imidazolidinedione, 5,5-diphenyl-imidazolidine-2,4-dione, phanantin, dintoin, and dillantin. The structure of phenyloin is shown in Formula II.

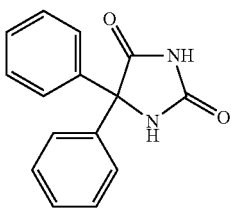

Formula II

A desirable feature of phenyloin for use in medical applications to aid in or accelerate wound healing is that it can be multi-functional or simultaneously provide more than one benefit. As discussed earlier, its functions include acting to stimulate tissue growth, as an analgesic to relieve local pain, as an agent to reduce transudation or exudation from wounds, and as an anti-inflammatory to reduce inflammation. Additionally it acts as an antimicrobial agent to reduce the bacteria load of wounds and/or tissue. By antimicrobial is meant it destroys microbes including bacteria, fungi, viruses and microbial spores preventing their development and pathogenic action.

According to the present invention, an effective amount of wound healing promoter, is incorporated into the pre-stabilized liquid monomeric cyanoacrylate adhesive compositions to form a homogeneous liquid adhesive product. The solid 5,5-disubstitutedhydantoin is added to the liquid cyanoacrylate monomers and this heterogeneous mixture is stirred at a mildly elevated temperature over a certain period to form a homogeneous mixture, as they are not soluble in cyanoacrylate monomers at room temperature.

Suitable temperatures range from about 40° C. to about 100° C., preferably from about 50° C. to about 90° C., more preferably from about 60° C. to about 90° C., and even more preferably from about 70° C. to about 80° C. After continuous stirring at this elevated temperature, the mixture of cyanoacrylate monomers and wound healing accelerator becomes a homogeneous solution within about 1 to 2 hours. Standard mixing equipment and techniques are suitable. The 5,5-disubstitutedhydantoins, including phenyloin are readily available from major chemical distributors.

According to embodiments of the present invention, the amount of 5,5-disubstitutedhydantoin incorporated into the cyanoacrylate composition will vary depending on the type of cyanoacrylate. Without being bound by a particular theory, it is believed that the shorter the cyanoacrylate side groups, the more wound healing accelerator can be dissolved into solution with the cyanoacrylate. When mixing with a 2-octylcyanoacrylate, generally, phenyloin is present in an amount of from about 0.05% to about 0.5%, preferably from about 0.05% to about 0.3% and more preferably from about 0.1% to 0.2%. (based on the total weight of all components in the solution). When mixed with n-butyl cyanoacrylate monomer, the phenyloin is present in an amount of from about 0.1% to about 1%, preferably from about 0.2% to about 0.8%, and more preferably from about 0.3 to about 0.5%. One skilled in the monomer and polymer field will be able, with some routine experimentation, to determine the amount of 5,5-disubstitutedhydantoin that can be added to the specific cyanoacrylate used.

One or more monomer may be included in the adhesive composition. Monomers that may be used in this invention are readily polymerizable, e.g., anionically polymerizable or free radical polymerizable, to form polymers. Preferred monomers include 1,1-disubstituted ethylene monomers of the formula III:

$$HRC=CXY \qquad (III)$$

wherein X and Y are each strong electron withdrawing groups, and R is H, —CH=CH$_2$, or provided that X or Y is a cyano group, R is a C$_1$-C$_4$ alkyl group.

Examples of monomers within the scope of formula (I) include alpha-cyanoacrylates, vinylidene cyanides, C$_1$-C$_4$ alkyl homologues of vinylidene cyanides, dialkyl methylene malonates, acylacrylonitriles, vinyl sulfinates and vinyl sulfonates of the formula CH$_2$=CX'Y wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (III) for use in this invention are alpha-cyanoacrylates. These monomers are known in the art and have the formula (IV):

(IV)

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2-4 carbon atoms, R$^5$ is an alkylene group having 2-12 carbon atoms, and R$^6$ is an alkyl group having 1-6 carbon atoms; or a group having the formula:

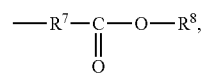

wherein R$^7$ is:

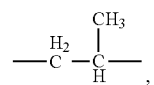

or —[C(CH$_3$)$_2$]$_n$—, wherein n is 1-10, preferably 1-8 carbon atoms and R$^8$ is an organic moiety.

Examples of suitable hydrocarbyl and substituted hydrocarbyl groups include straight chain or branched chain alkyl groups having 1-16 carbon atoms; straight chain or branched chain $C_1$-$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; arylalkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$-$C_8$ alkyl moieties, $C_2$-$C_8$ alkenyl moieties, $C_2$-$C_8$ alkynyl moieties, $C_3$-$C_{12}$ cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromo-substituted hydrocarbons) and oxy-(e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 8 carbon atoms.

In the cyanoacrylate monomer of formula (IV), $R^3$ is preferably an alkyl group having 1-10 carbon atoms or a group having the formula -$AOR^9$, wherein A is a divalent straight or branched chain alkylene or oxyalkylene moiety having 2-8 carbon atoms, and $R^9$ is a straight or branched alkyl moiety having 1-8 carbon atoms. Examples of groups represented by the formula -$AOR^9$ include 1-methoxy-2-propyl, 2-butoxy ethyl, isopropoxy ethyl, 2-methoxy ethyl, and 2-ethoxy ethyl. The preferred alpha-cyanoacrylate monomers used in this invention are 2-octyl cyanoacrylate and butyl cyanoacrylate.

In preferred embodiments of the present invention, the cyanoacrylate monomers can be prepared according to methods known in the art, for example, U.S. Pat. Nos. 2,721,858 and 3,254,111, each of which is hereby incorporated in its entirety by reference. One such process includes, for example, reacting a cyanoacetate with formaldehyde in the presence of a basic condensation catalyst at an elevated temperature to produce a low molecular weight polymer. A depolymerization (or cracking) step is followed under high temperature and high vacuum in the presence of acidic and anionic inhibitors, yielding a crude monomer that can be distilled under high temperature and high vacuum in the presence of radical and acidic inhibitors. In preferred embodiments, the distilled 2-cyanoacrylate monomers are then formulated with free radical and acidic inhibitors to provide the necessary stability and other desired physical properties.

Without proper stabilization, the premature polymerization of cyanoacrylate could be induced by 5,5-disubstitutedhydantoin. In order to prevent the premature polymerization of cyanoacrylate monomers when heating to dissolve the wound healing accelerator, and provide long term stability of cyanoacrylate formulations containing the accelerator, cyanoacrylate monomers are stabilized with the combination of free radical and anionic stabilizers before the addition of the 5,5-disubstitutedhydantoin ("pre-stabilized"). In embodiments of the present invention, the preferred primary free radical stabilizer is butylated hydroxyl anisole (BHA). Other free radical stabilizers include without limitation, hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tertbutyl-4-methoxyphenol; 2-tert-butyl-4-methoxyphenol; 2,2-methylene-bis-(4-methyl-6-tert-butylphenol).

The amount of stabilizer to be used can be determined by one of ordinary skills in the art using known techniques without undue experimentation. MP is used in an amount of about 1 ppm to about 4000 ppm, preferably about 100 to about 2000 ppm. Hydroquinone is, used in an amount of about 1 ppm to about 2500 ppm, preferably from about 50 ppm to about 1500 ppm. BHT is used in an amount of about 1 ppm to about 10000 ppm, preferably from about 500 ppm to about 5000 ppm.

According to some embodiments of the present invention, the preferred anionic stabilizer is sulfur dioxide in an amount of about 2 ppm to about 500 ppm, preferably about 10 ppm to about 200 ppm to pre-stabilize cyanoacrylate monomers before adding 5,5-disubstitutedhydantoin. Other anionic stabilizers may be a very strong acid including without limitation perchloric acid, hydrochloric acid, hydrobromic acid, toluenesulfonic acid, fluorosulfonic acid, phosphoric acid, ortho, meta, or para-phosphoric acid, trichloroacetic acid, and sulfuric acid. The very strong acid is used in an amount of about 1 ppm to about 250 ppm, preferably from about 5 ppm to about 50 ppm.

The compositions of the present invention generally contain the wound healing accelerator and a stabilized polymerizable monomer. The polymerizable monomer, and the composition as a whole, are in liquid form and provide adhesive properties. Other components, known in the art, may also be included in the composition for their known effects and in known amounts.

According to some embodiments of the present invention, the compositions may optionally contain thickening agents. Suitable thickening agents include polycyanoacrylate, partial polymer of cyanoacrylate, polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, and triblock copolymers of polyoxypropylene flanked by two hydrophilic chains of polyoxyethylene. The preferred thickening agents are a partial polymer of cyanoacrylate as disclosed in U.S. Patent Application Publication No. 2009/0318583, and triblock copolymers of polyoxyalkylene as disclosed in U.S. Patent Application Publication No. 2009/0317353. Preferably the thickening agent is miscible in cyanoacrylate monomer compositions at room temperature.

In certain embodiments of the present invention, the composition may include a polymerization accelerator. Suitable polymerization accelerators are calixarenes and oxacalixarenes, silacrowns, crown ethers, cyclodextrin and its derivatives, polyethers, aliphatic alcohol, various aliphatic carboxylic acid esters, benzoyl peroxide, amine compounds such as triethyl amine, diethyl amine, butyl amine, isopropyl amine, tributyl amine, N,N-dimethyl aniline, N,N-diethyl aniline, N,N-dimethyl-p-toluidine, N,N-dimethyl-m-toluidine, N,N-dimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts such as alkylammonium salts, amide-bonded ammonium salts, ester-bonded ammonium salts, salts and alkylimidazolinium salts, cyclosulfur compounds and derivatives, and polyalkylene oxides and derivatives.

Suitable crown ethers include, but are not limited to, 15-crown-5; 18-crown-6; dibenzo-18-crown-6; tribenzo-18-crown-6; dicyclohexyl-18-crown-6; benzo-15-crown5; dibenzo-24-crown-8; dibenzo-30-crown-10; asym-dibenzo-22-crown-6; dimethylsila-11-crown-4; dimethylsila-14-crown-5; dimethylsila-17-crown-6; dibenzo-14-crown-4; dicyclohexyl24-crown-8; asym-dibenzo-22-crown-6; cyclohexyl-12-crown-4; 1,2-decalyl-15-crown-5; 1,2naphtho-15-crown-5; 3,4,5-naphthyl-16-crown-5; 1,2-methyl-benzo-18-crown-6; 1,2-methylbenzo-5,6-methylbenzo-18-crown-6; 1,2-t-butyl-18-crown-6,1,2-vinylbenzo-15-crown-5; 1,2-vinylbenzo-18-crown-6; 1,2-t-butyl-cyclohexyl-18-crown-6; and 1,2-benzo-1,4-benzo-5oxygen-20-crown-7. The preferred crown ether is 18-crown-6.

Suitably, the crown ether is used in an amount of up to 2000 ppm, preferably 50 to 1000 ppm, and more preferably 100 to 500 ppm. The amount to be used can be determined by one of ordinary skill in the art using known techniques and without undue experimentation.

The compositions of this invention may further contain small amounts of colorants such as dyes, pigments, and pigment dyes. Suitable dyes include derivatives of anthracene and other complex structures. These dyes include without limitation, 1-hydroxy-4-[4-methylphenylamino]-9,10 anthracenedione (D&C violet No. 2); 9-(o-carboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); 2(1,3-dihydro-3-oxo-5-sulfo-2H-indole-2-ylidine)-2,3-dihydro-3-oxo-1H-ind-ole-5 sulfonic acid disodium salt (FD&C Blue No. 2); and 1,4-bis(4-methylanilino)anthracene-9,10-dione (D&C Green No. 6).

According to certain embodiments of the present invention, a plasticizer may be included in the inventive cyanoacrylate compositions. The plasticizing agent preferably does not contain any moisture and should not adversely affect the stability of the cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl)phosphate, tri(p-cresyl) phosphate, diisodecyl adipate (DIDA); glyceryl triacetate, glyceryl tributyrate, dioctyl adipate (DICA), isopropyl myrisate, butyl sterate, lauric acid, trioctyl trimelliate, dioctyl glutatrate (DICG) and mixtures thereof. Tributyl citrate, diisodecyl adipate and acetyl tributyl citrate are preferred plasticizers used in an amount of 0 to 30%, preferably 1% to 20%, and more preferably 2% to 10%.

As discovered in the present invention, the 5,5-disubstitutedhydantoin incorporated into cyanoacrylate monomers at the elevated temperature, does not precipitate from the cyanoacrylate monomers after the solution is cooled down to room temperature. This observation is important since the homogeneous solution of the healing accelerator in cyanoacrylate monomers at room temperature can achieve even distribution on the tissue and more effective medicament delivery to the target site.

Table 1 below summarizes the results of incorporating phenyloin into different cyanoacrylate monomer solutions at the elevated temperatures. As shown in Table 1, phenyloin is not soluble in 2-octyl cyanoacrylate (OCA) monomer at room temperature. At the elevated temperatures, phenyloin is soluble in both 2-octyl cyanoacrylate (OCA) and n-butyl cyanoacrylate (BCA). It is also interesting to note that phenyloin is more soluble in shorter alkyl chain cyanoacrylate (BCA) than in longer alkyl chain cyanoacrylate (OCA).

TABLE 1

Incorporation of phenytoin into different cyanoacrylates.

| Formulation | OCA | BCA | Phenytoin | Mixing temperature (° C.) | Miscibility |
|---|---|---|---|---|---|
| 1a | 100% | 0% | 0.50% | RT | Not soluble |
| 1b | 100% | 0% | 0.12% | 80 | Soluble |
| 1c | 80% | 20% | 0.15% | 70 | Soluble |
| 1d | 0 | 100% | 0.30% | 80 | Soluble |

The stability of the inventive liquid monomeric cyanoacrylate adhesive compositions containing phenyloin was confirmed by accelerated aging testing, which was performed in an oven at 80° C. for a period of about 13 days. Based on calculations, 13 days of accelerated aging at 80° C. is equal to 2 years of shelf life, and 1 day of accelerated aging at 80° C. is equal to about 56 days. Throughout the entire aging test procedure, all cyanoacrylate adhesive samples containing phenyloin remained in a fluid consistency. Viscosity was the measure of stability (industry standard) and the stability of the samples is set forth below in Table 2. The viscosity of the cyanoacrylate compositions containing phenyloin were measured by a Brookfield DV-II+ Pro viscometer. The spindle and sample chamber were cleaned with acetone after each measurement. About 7 ml of the cyanoacrylate composition was put into the sample chamber and the chamber was brought into position. The motor was turned on after the sample was equilibrated in the sample chamber. The viscosity of the disclosed composition was measured in triplicate. Any residue was removed with acetone prior to the next sample measurement.

TABLE 2

Viscosities of cyanoacrylate adhesive compositions containing phenytoin before (Day 0) and after the accelerated aging test at 80° C.

| Formulation | Amount of Phenytoin | Cyanoacrylate | Average viscosity before and after accelerated aging (cps) | | | |
|---|---|---|---|---|---|---|
| | | | Day 0 | Day 3 | Day 6 | Day 13 |
| 2a | 0.1% | OCA | 6.07 | 6.72 | 7.29 | 8.80 |
| 2b | 0.1% | OCA/BCA 4:1 | 5.32 | 4.32 | 6.07 | 8.66 |
| 2c | 0.15% | OCA | 6.84 | 7.95 | 9.50 | 22 |
| 2d | 0.15% | OCA/BCA 4:1 | 5.38 | 5.58 | 6.40 | 7.47 |
| 2e | 0.12% | OCA | 7.57 | 8.27 | 9.02 | 16.57 |
| 2f | 0.12% | OCA/BCA 4:1 | 5.32 | 5.74 | 6.39 | 6.82 |
| 2g | 0.12% | BCA | 4.77 | 5.27 | 5.58 | 10.13 |
| 2h | 0.30% | BCA | 5.36 | 5.96 | 6.46 | 8.74 |

The viscosity of the cyanoacrylate adhesive composition containing phenyloin increased as the accelerated aging proceeded but the viscosity of the aged samples after day 13 was within an acceptable range which does not affect the ability to dispense the adhesive from the applicator. Actually, the increase of the viscosity of the most preferred cyanoacrylate adhesive compositions (a, b, d, f, and h) after the accelerated aging test is very little, indicating that the said adhesive compositions were stable.

According to the present invention, any suitable applicator can be used to store and apply the composition to the affected areas of skin. Suitable applicators and packaging systems may be any container which maintains the sterility and integrity of its contents. The preferred container is also one which is compatible with the chosen method of sterilization, including irradiation. The materials comprising the suitable container are desirably irradiation stable under the maximum dosage of the sterilization. The suitable container also desirably provides a barrier to moisture so that it is compatible with the cyanoacrylate monomer compositions. Suitable applicators may be in any container configuration such as, but not limited to a swab, vial, pouch, syringe, ampoule, or bottle, having an appropriate means, surface or tip to dispense the cyanoacrylate compositions from the container and apply onto the skin.

In embodiments, a preferred package or container for the compositions of the instant invention has multiple layers of different materials, including polymers and metal. Most preferred is a container wherein the inner layer is a nitrile polymer and the outer layer is polypropylene. The suitable package body may also be composed of an inner layer of nitrile polymer and an outer layer of aluminum. The nitrile polymer material is preferably a copolymer composition, specifically, 2-propenoic acid, methyl ester, polymer with 1,3-butadiene and 2-propenenitrile, sold under the "BAREX" brand by BP Petrochemicals. BAREX® polymer provides high barrier properties which ensure the stability of the cyanoacrylate adhesive product stored therein. The exceptional barrier properties offered by BAREX® polymers make them an ideal inner layer material for use in construction of package bodies in accordance with the present invention. BAREX® polymers offer a high barrier to oxygen at all levels of relative humidity. This ensures that a consistently high barrier to oxygen is maintained, regardless of the humidity of the surrounding environment. In addition, the water vapor barrier properties of BAREX® polymers are comparable to other plastic packaging materials and are ultimately enhanced by the outer layer secured thereto in accordance with the present invention.

The present invention, in embodiments, is applicable to single-use containers and may be applicable to applicators, where it is desired to maintain a high degree of prolonged sterility and stability of the composition, by supplementing an optional sterilization treatment by addition of the wound healing agent. Likewise, in embodiments, the present invention may also be suited for multiple-use containers or applicators, where it is desired to maintain a high degree of prolonged sterility and stability of the composition against microbial action despite loss of initial sterility upon first use of the composition.

The antimicrobial properties of the wound healing agent of the present invention may operate to destroy microorganisms that may be present or grow in the polymerizable monomer composition prior to use of the composition. The antimicrobial properties of the wound healing agent of the present invention operates to destroy microorganisms in and around the application site subsequent to polymerization of the composition on the desired application site such as a wound or incision. As set forth above, many antimicrobial agents also function as polymerization inhibitors, however, the wound healing agent of the instant invention does not operate as such and does not affect polymerization of the monomer material.

Cyanoacrylate adhesive compositions for medical application are preferably sterile. Sterilization of the monomer composition and/or its container and/or packaging can be accomplished by any method, including, but not limited to chemical, physical and irradiation techniques. Examples of chemical methods include, but are not limited to, exposure to ethylene oxide and hydrogen peroxide. Examples of physical methods include, but are not limited to, sterilization by heat (dry or moist) or retort canning. Examples of irradiation methods include, but are not limited to, gamma irradiation, electron beam irradiation, and microwave irradiation. Preferred methods of sterilization are chemical and irradiation methods, including but not limited to, electron beam (E-beam), gamma irradiation and X-Ray.

When sterilizing the compositions using E-beam irradiation, the dose applied which is sufficient enough to sterilize the adhesive compositions, typically, ranges from about 5 kGy to 50 kGy, and more preferably from about 12 kGy to 25 kGy. E-beam irradiation is preferably conducted at ambient atmosphere conditions and the exposure time to the irradiation is preferably within 60 seconds. Any standard power source is suitable, including a linear accelerator, which produces irradiation measured in kilo watts (KW). The larger the beam power, the more product volume can be processed. The inventive cyanoacrylate adhesive compositions are irradiated at a beam power ranging from about 2 KW to about 30 KW, preferably about 5 KW to about 20 KW, and more preferably about 10 KW to about 20 KW. E-beam irradiation typically involves the use of high-energy electrons. The beam energy ranges from 1 million to 10 million electron volts (MeV), preferably 3 MeV to 10 MeV, and more preferably 5 MeV to 10 MeV.

In order to reduce the bioburden, the inventive cyanoacrylate adhesive compositions may be filtered through a 0.2 μm filter prior to E-beam sterilization. The inventive adhesive compositions may also be sterilized with heat or ethylene oxide prior to the final E-beam irradiation.

In preferred embodiments of the present invention, the composition is sterilized to provide a Sterility Assurance Level (SAL) of at least $10^{-3}$. This means that the probability of a single unit being non-sterile after sterilization is 1 in 1000. In more preferred embodiments, the sterility assurance level may be at least $10^{-4}$, $10^{-5}$, or $10^{-6}$. After sterilizing the inventive cyanoacrylate adhesive compositions, their sterility levels were analyzed by Bacteriostasis and Fungistasis tests. After testing with challenging microorganisms such as *Bacillus subtilis*, *Candida albicans*, and *Aspergillus niger*, no growth of the microorganisms was observed, indicating the sterility of the inventive compositions.

Table 3 below shows the viscosity of some preferred cyanoacrylate compositions, the same as in Table 2, before and after sterilization with E-beam irradiation. No significant change in the viscosity of the inventive compositions, was observed upon sterilization. The viscosity of these compositions increased only slightly after sterilization, indicating that the effect of sterilization on the compositions is insignificant.

TABLE 3

Viscosity of the cyanoacrylate adhesive compositions containing phenytoin before and after sterilization.

| | Viscosity (cps) | |
|---|---|---|
| Formulation | Before sterilization | After sterilization |
| 2a | 6.07 | 6.94 |
| 2b | 5.32 | 6.04 |
| 2d | 5.38 | 6.12 |
| 2f | 5.32 | 6.33 |

The changes in viscosity as measured before and after sterilization of the inventive compositions are desirably between about 0% and 100%, preferably between about 0% and about 80% and more preferably between about 0% and about 40%. It is an advantage of the current invention that the integrity of the adhesive composition is maintained upon sterilization, as it has been reported in the literature that the viscosity of cyanoacrylate compositions often changes after sterilization. Cyanoacrylate adhesives reported in the prior art have demonstrated a 400% increase or more in viscosity induced by sterilization. And, often sterilization is used to intentionally increase the viscosity of cyanoacrylate adhesives. The compositions and method of making the compositions of the present invention minimize the variation in viscosity of cyanoacrylate adhesives otherwise observed due to sterilization.

Typically, for medical purposes, an adhesive should have a shelf-life of at least one year; however, an increased shelf-life beyond this provides increased economic advantages to both the manufacturer and the consumer. As used herein, shelf-life refers to the amount of time the container and composition therein can be held at ambient conditions (approximately room temperature) or less, without degradation of the composition and/or container occurring to the extent that the composition and container cannot be used in the manner and for the purpose for which they were intended. Thus, while some degradation to either or both of the composition and container can occur, it must not be to such an extent that the composition and/or container are no longer useable. As used herein, an "extended shelf-life" refers to a shelf-life of at least 12 months, preferably at least 18 months, more preferably at least 24 months, and even more preferably, at least 30 months.

To assess the stability of some of these same formulations as above after sterilization, an accelerated aging test was performed. As used herein "stability" refers to the resultant composition maintaining a commercially acceptable form for the prescribed amount of time. That is, the composition does not prematurely polymerize or otherwise change form or degrade to the point that the composition is not useful for its intended purpose. Thus, while some polymerization or thickening of the composition may occur, such as can be measured by changes in viscosity of the composition, such change is not so extensive as to destroy or significantly impair the usefulness of the composition. The accelerated aging test was performed in the oven at 80° C. for a period of 13 days. Based on calculations, 13 days accelerated aging at 80° C. is equal to 2 years of shelf life, and 1 day of accelerated aging at 80° C. is equal to 56 days. Throughout the entire aging procedure, all cyanoacrylate adhesive samples retained fluid consistency and good color. The stability of the aged samples was confirmed by viscosity tests. The viscosity of the cyanoacrylate adhesive compositions slightly increased as the accelerated aging proceeded indicating very little premature polymerization of the cyanoacrylate compositions occurred upon sterilization making them particularly suitable for medical applications. The average viscosity of the compositions at accelerated aging day 0, day 3, day 6, day 10, and day 13 was 6.04, 7.66, 9.91, 14.8, and 24.7 centipoise (cps), respectively. Additionally, it is expected that this slight increase in viscosity at the end of the accelerated aging will not affect the performance of the cyanoacrylate adhesives nor the ability of the compositions to dispense from the applicator, indicating these sterilized cyanoacrylate compositions provide a shelf life of at least two years.

Accordingly, the instant inventive adhesive compositions containing a 5,5-disubstitutedhydantoin, provide a stable shelf life for use in the medical field. The stability, and thus the shelf-life, of the inventive cyanoacrylate adhesive compositions were maintained during the accelerated aging tests, the packaging and sterilizing procedures. In preferred embodiments, there is substantially no significant polymerization of the monomeric liquid adhesive compositions that could affect the utility of the monomer.

Suitable ranges for the set time of the cyanoacrylate compositions of the instant invention is in the range from about 5 to about 120 seconds, more preferably from about 10 to about 80 seconds, and even more preferably from about 15 to about 70 seconds.

The present invention further provides a kit for applying the cyanoacrylate adhesive composition containing 5,5-disubstitutedhydantoin as the wound healing accelerator, including an applicator containing therein an effective amount of the cyanoacrylate composition. Any suitable applicator can be used to apply the inventive composition to the affected areas of skin. Suitable applicators may be any container such as, but not limited to, a swab, a vial, or any configuration having an appropriate means, surface or tip to store and deliver the cyanoacrylate compositions from the container. The kit can further contain other appropriate practical elements to suit specific uses, including but not limited to surgical tools, other medicaments and directions for application. When the present invention is used with other therapeutics or medicaments separate containers can be provided for the cyanoacrylate composition and the therapeutic. Individual applicators can be packaged separately to maintain sterile conditions. For example, each applicator can be packaged in plastic or any other suitable enclosing material. Multiple applicators can then be packaged in a box for shipping.

The cyanoacrylate compositions of the present invention are particularly suitable for use in medical application in terms of promoting wound healing. In use, the cyanoacrylate adhesive composition is applied as a liquid to tissue to be sealed and then allowed to polymerize upon contact with tissue to form an antimicrobial barrier film. The 5,5-disubstitutedhydantoin incorporated within cyanoacrylate compositions can accelerate the wound healing process during and following its application to the skin.

Additional objects, advantages, and novel features of this invention will become apparent to those skilled in the art upon examination of the following examples of the invention. The examples are included to more clearly demonstrate the overall nature of the invention and, thus, are illustrative and not restrictive of the invention.

The shelf life stability of the inventive cyanoacrylate compositions was evaluated by an accelerated aging test. 13 days of accelerated aging at 80° C. is equal to 2 years at room temperature. The samples of the cyanoacrylate monomers containing phenyloin were placed in the oven at 80° C. Samples were taken at day 3, day 6, day 10 and day 13 for the measurement of viscosity and set time to evaluate the stability of the said adhesives.

The viscosity of the cyanoacrylate compositions containing phenyloin were measured by a Brookfield DV-II+ Pro viscometer. The spindle and sample chamber were cleaned with acetone after each measurement. About 7 ml of the cyanoacrylate composition was put into the sample chamber and the chamber was brought into position. The motor was turned on after the sample was equilibrated in the sample chamber. The viscosity of the disclosed composition was measured in triplicate. Any residue was removed with acetone prior to the next sample measurement.

Set time was measured using pig skin (4×4 square inch) prepared by wiping the surfaces of the skin with sterile gauze saturated with isopropanol. All oily substances were thereby removed from the pig skin. The surface was then wiped with sterile gauze to remove the isopropanol. A thin film of the cyanoacrylate composition was applied to the pig skin after which elapsed time was recorded by a stop watch. Set time was then recorded by stopping the clock when the film was dry as determined at the point where no liquid transfer occurred when the film was touched with a gloved finger.

EXAMPLES

Example 1

To a three neck round bottom flask equipped with a thermometer and a magnetic stir bar, 118.7 g of 2-octyl cyanoacrylate monomer containing 270 ppm of 18-crown-6 was stabilized with BHA and $SO_2$, which was mixed with 0.12 g of phenyloin and stirred at 80° C. for about 2 hours. After it cooled down, no precipitate was observed and the resulting cyanoacrylate composition was a clear and homogeneous solution.

Example 2

A mixture of cyanoacrylate monomer including 80% 2-octyl cyanoacrylate and 20% n-butyl cyanoacrylate was stabilized with BHA and $SO_2$.251.1 g of such mixture of cyanoacrylate was mixed with 0.25 g of phenyloin in a three neck round bottom flask. The resulting heterogeneous mixture was heated to 78° C. and stirred for about an hour until all phenyloin was dissolved in the cyanoacrylate monomers. After cooling down to room temperature, the homogenous solution was stirred overnight at room temperature to check the miscibility of phenyloin with cyanoacrylate monomers. 10 ppm of SO2 was added to the solution to stabilize the cyanoacrylate composition containing phenyloin.

Example 3

To a three neck round bottom flask equipped with a thermometer and a magnetic stir bar, 115.6 g of n-butyl cyanoacrylate monomer stabilized with BHA and $SO_2$ was mixed with 0.35 g of phenyloin and stirred at 80° C. until all visible solid particles of phenyloin were dissolved in n-butyl cyanoacrylate. After it cooled down, no precipitate was observed and the resulting cyanoacrylate composition was a clear and homogeneous solution. The viscosity and set time of the resulting composition was 5.36 cps and 14 seconds, respectively.

Example 4

115.8 g of 2-octyl cyanoacrylate monomer with BHA and $SO_2$ as the free radical and anionic stabilizers, respectively, was mixed with 0.116 g of phenyloin in a three neck round bottom flask. The resulting mixture was stirred at 70° C. for about 1 hour until all of the phenyloin white powder was dissolved in the 2-octyl cyanoacrylate monomer to prepare cyanoacrylate compositions containing phenyloin. After the solution was cooled to room temperature, no precipitate of phenyloin was observed.

While the invention has been described with reference to preferred embodiments, the invention is not limited to the specific examples given, and other embodiments and modifications can be made by those skilled in the art without departing from the spirit and scope of the invention.

What is claimed is:

1. A monomeric adhesive composition, comprising an alpha cyanoacrylate monomer selected from the group consisting of 2-octyl cyanoacrylate, n-butyl cyanoacrylate, and a mixture that is 80% by weight 2-octyl cyanoacrylate and 20% by weight n-butyl cyanoacrylate, an amount of butylated hydroxyl anisole and sulfur dioxide effective to stabilize the alpha cyanoacrylate monomer, and 0.05% to 0.3% by weight of the composition of phenytoin; wherein the composition is a homogeneous mixture, wherein the composition is packaged in an applicator having an inner layer comprising a nitrile polymer and an outer layer comprising polypropylene or aluminum and sterilized, and wherein the sterilized composition remains in a fluid consistency in the applicator following accelerated aging testing at 80 degrees C.

2. A method of treating tissue comprising applying the adhesive composition of claim 1 to a tissue surface, and allowing said composition to polymerize on said tissue surface.

3. A polymer film formed by polymerizing the composition of claim 1.

4. The monomeric adhesive composition of claim 1, further comprising a polymerization accelerator.

5. The monomeric adhesive composition of claim 1, further comprising a plasticizing agent.

6. The monomeric adhesive composition of claim 1, further comprising a thickening agent.

7. The monomeric adhesive composition of claim 1, wherein the composition is sterilized by irradiation.

8. The monomeric adhesive composition of claim 7, wherein the composition is sterilized by electron beam (E-beams) irradiation.

9. The monomeric adhesive composition of claim 1, wherein the viscosity of the composition increases between 0% and 40% following sterilization.

10. The monomeric adhesive composition of claim 1, wherein the composition has a shelf life of at least 24 months.

11. The monomeric adhesive composition of claim 1, wherein the composition comprises 2-octyl cyanoacrylate and an amount of butylated hydroxyl anisole and sulfur dioxide effective to stabilize the 2-octyl cyanoacrylate, homogenously mixed together with 0.1% to 0.2% by weight of the composition of phenytoin.

* * * * *